United States Patent
Müller et al.

(10) Patent No.: US 7,474,403 B2
(45) Date of Patent: Jan. 6, 2009

(54) DEVICE AND METHOD FOR MEASURING THE OPTICAL PROPERTIES OF AN OBJECT

(75) Inventors: Jürgen Müller, Hamburg (DE); Norbert Gorbow, Hamburg (DE)

(73) Assignee: Evotec Technologies GmbH, Duesseldorf (DE)

(*) Notice: Subject to any disclaimer, the term of this patent is extended or adjusted under 35 U.S.C. 154(b) by 302 days.

(21) Appl. No.: 10/577,868

(22) PCT Filed: Oct. 29, 2004

(86) PCT No.: PCT/EP2004/012309

§ 371 (c)(1), (2), (4) Date: Apr. 28, 2006

(87) PCT Pub. No.: WO2005/043213

PCT Pub. Date: May 12, 2005

(65) Prior Publication Data

US 2007/0035734 A1 Feb. 15, 2007

(30) Foreign Application Priority Data

Oct. 31, 2003 (DE) ............................... 103 50 918

(51) Int. Cl.
- *G01N 21/59* (2006.01)
- *G01N 21/64* (2006.01)
- *G02B 27/40* (2006.01)
- *G02B 26/08* (2006.01)

(52) U.S. Cl. ............... 356/432; 250/363.1; 250/201.3; 250/458.1; 359/196; 359/204

(58) Field of Classification Search ......... 356/432–444, 356/317–320; 250/201.3, 251, 458.1, 459.1; 359/204, 214, 226, 372, 385
See application file for complete search history.

(56) References Cited

U.S. PATENT DOCUMENTS

| | | | | |
|---|---|---|---|---|
| 6,020,591 A | * | 2/2000 | Harter et al. | 250/458.1 |
| 6,369,928 B1 | * | 4/2002 | Mandella et al. | 359/204 |
| 6,388,788 B1 | * | 5/2002 | Harris et al. | 359/196 |
| 6,582,903 B1 | * | 6/2003 | Rigler et al. | 435/6 |
| 6,677,566 B2 | * | 1/2004 | Knebel et al. | 250/201.3 |
| 7,166,846 B2 | * | 1/2007 | Engdahl et al. | 250/363.1 |
| 7,180,661 B2 | * | 2/2007 | Sasaki | 359/385 |

FOREIGN PATENT DOCUMENTS

EP  1283416  2/2003

* cited by examiner

*Primary Examiner*—Sang Nguyen
(74) *Attorney, Agent, or Firm*—Ohlandt, Greeley, Ruggiero & Perle, L.L.P.

(57) ABSTRACT

A device for measuring the optical properties of an object, particularly of a chemical and/or biological sample, comprises an illumination light source for illuminating the object. Further, an excitation light source is provided for illuminating the object, wherein the radiation of the excitation light source being suited to change the optical properties of the object. Further, the excitation radiation is focused in a measurement volume arranged within the object. By means of a detector device, there can be detected preferably the transmission of the illumination radiation through the object within the measurement volume.

17 Claims, 2 Drawing Sheets

DEVICE AND METHOD FOR MEASURING THE OPTICAL PROPERTIES OF AN OBJECT

FIELD OF THE INVENTION

The invention relates to a device and a method for measuring optical properties of an object, preferably for measuring the optical transmission or absorption properties of the object. Particularly, the object can be a chemical and/or biological sample which preferably comprises particles such as cells.

DISCUSSION OF THE BACKGROUND ART

For examining the transmission properties of objects, it is known to illuminate the sample both by an excitation light source, also referred to as a pump light source, and by an illumination light source, also referred to as a sample light source. The light can be visible light or non-visible light. In the process, the molecules of the object under examination are excited by the excitation light source so that the population density of the basic state of the molecule is reduced. By use of the illumination light source, the condition of the molecules can be analyzed in different manners. For instance, there is known the possibility to select the wavelength of the illumination light source to be similar to that of the excitation light source. This has the consequence that the radiation coming from the illumination light source will not be taken up anymore by the already excited molecules and thus, under the influence of the excitation radiation, the transmission of the illumination radiation through the object is increased. On the other hand, the wavelength of the illumination radiation can be selected to be similar to the emission wavelength of the excited molecules. In this case, the illumination radiation can cause the stimulated emission of photons in the molecules excited by the excitation radiation. This will result in a seemingly increased transmission of the illumination radiation because of the occurrence of additional photons emitted in the object which have the same wavelength. A further known possibility resides in selecting the wavelength of the illumination radiation to the effect that the wavelength can be preferably absorbed by such molecules which are already in the condition excited by the excitation radiation. In this case, the excitation of the molecules by the excitation radiation will effect a decrease of the transmission of the illumination radiation. In the known methods, both the illumination light source and the excitation light source are focused at the same site on the object. In this case, to be able to use a common optics system, both light sources are arranged on the same side of the object. A detector device is located on the opposite side of the object for measuring the transmission.

To make it possible to perform a three-dimensionally spatially resolved measurement within an object, a confocal configuration is of advantage. In this regard, a variety of optical arrangements are known:

In confocal microscopy where typically only one light source is used, it is known to arrange an optics system and a pinhole in front of the detector and to adjust them in such a manner that the detector will preferably receive light from that measurement volume which also lies in the focus of the light source. In such an arrangement, the illumination radiation and the detection radiation are guided through the same optics system.

It is also known, in case that separate excitation and illumination light sources are used, that these light sources can be focused by a common optics system onto a common measurement volume. As a result of the preferred illumination of the measurement volume by both light sources, the three-dimensional spatial resolution of the measurement will be guaranteed already on the side of the illumination; in this case, the detector does not necessarily have to be a spatially resolving detector. However, this arrangement suffers from the basic disadvantage that a parallelized measurement, i.e. a simultaneous measurement of a plurality of measurement volumes in the object, is not possible because the detector will always capture the light of all measurement volumes together and a spatial assignment will not be possible.

It is an object of the invention the provide a device and a method for measuring optical properties of an object, preferably for measuring the optical transmission properties of the object, which method and device make it possible to perform a parallelized measurement of a plurality of measurement volumes.

SUMMARY OF THE INVENTION

The inventive device for measuring optical properties of an object, particularly of a chemical and/or biological sample comprising particles such as cells and the like, is suited particularly for measuring the optical transmission and absorption properties of the object. The device comprises an illumination light source for illumination of the object. The illumination light source is particularly a broad-band light source, e.g. a mercury or xenon lamp followed by a filter for selection of a spectral region. By way of alternative, use can be made of a laser source with suitable beam-widening optics. Further, the device comprises an excitation light source which is preferably a laser light source. The excitation light source is suited, by means of the radiation used, to change the optical characteristics of the object. In doing so, the excitation light source will particularly change the population density of the basic condition of the molecules under examination. Further, the device comprises a detection unit such as e.g. a CCD array, for detecting the radiation emitted by the object. The radiation in this case can be particularly the radiation of the illumination light source passing through the object so that a transmission light measurement will be performed. According to the invention, the illumination light source will illuminate a spatially dimensioned portion of the object. Thus, the illumination light source is not focused on the measurement volume or the individual measurement volumes within the object. The excitation light source, on the other hand, is focused onto at least one measurement volume and preferably a plurality of measurement volumes. Thus, the excitation light source will preferably illuminate a plurality of small measurement volumes at the same time. Here, the illumination of the individual measurement volumes is performed on the object plane imaged on the detector device. The portion of this object plane imaged onto the detector device is at least partially congruent with the object portion which is illuminated by the illumination light source. The provision of a spatially resolving detector such as e.g. a CCD array or also of individual detectors makes it possible to examine preferably the transmission through the individual measurement volumes. Thus, the device of the invention can be used to examine a plurality of individual measurement volumes of the sample in parallel.

For generating a plurality of measurement volumes in the object plane imaged on the detector device, an array of pinholes (apertures) arranged on a rotating so-called Nipkow disk can be imaged into the object. To increase the excitation efficiency, a microlens array can be provided within the excitation beam path upstream of the pinhole array for focusing the excitation radiation onto the individual pinholes.

With particular preference, a confocal detection is carried out. For this purpose, according to the invention, the beam path upstream of the detector device is provided with a pinhole or—in case of a plurality of measurement volumes—a pinhole array, possibly in combination with one or a plurality of lenses. In such an arrangement, the pinhole array provided on the detection side corresponds to the pinhole array assigned to the excitation light source, or it corresponds to the Nipkow disk provided there. Particularly, it is preferred that the detection beam path is guided through the same pinhole array as the excitation beam path so that, without expenditure for adjustment, there is obtained a precise spatial congruence between the pinholes acting on the excitation and the detection sides. Alternatively, it can be provided according to the invention to use a detection-side pinhole array which will correspond with an array of microlenses arranged on the excitation side. In this case, the microlens array serves for generating the measurement volumes.

The measurement volume or the individual measurement volumes are approximately dot-shaped. Particularly, the volume of an individual measurement volume is smaller than $(100\ \mu m)^3$, particularly smaller than $(10\ \mu m)^3$. Instead of providing a Nipkow disk or the like, it is also possible to move an individual measurement volume relative to the object, so that a scanning of the object is performed. Further, a corresponding combination is possible.

A further possibility consists in generating one or a plurality of linear measurement volumes, e.g. by use of cylindrical lenses and/or line apertures which can be arranged e.g. on a rotating disk. Further, it is possible to move the linear measurement volume vertically to the line so that a scan movement of the line is carried out in the object plane.

For performing different examinations, it is preferably possible to vary the properties of the illumination light source and/or the excitation light source. For this purpose, a variation of the wavelength and/or the intensity can be performed. Particularly, the illumination light source and/or the excitation light source is spectrally variable and/or selectable.

The detector device, which is preferably provided as a CCD array with high local resolution and which, if required, comprises additional elements for selection of the detection wavelength range, is preferably fast-readable and/or readable in a pixel-selective manner. Particularly, the individual pixels are readable within less than 10 $\mu s$, preferably less than 1 $\mu s$. As a CCD array, preferred use is made of the CCD camera "SensiCam QE" manufactured by PCO GmbH. Further, preferably, the sensitivity of the detector is variable or adjustable. Also, a suitable control unit can be provided for detecting the detector signals of individual pixels or groups of pixels in dependence on the phase relationship between the modulations of the intensity of the illumination light sources.

With particular preference, use is made of a detector device having a selectable spectral sensitivity. This offers the possibility to detect either the transmitted illumination radiation or the fluorescence radiation emitted by the object.

Preferably, the illumination light source is switchable or adjustable in its radiation intensity. Thereby, it is possible, particularly in connection with the above described detector device, to measure both the fluorescence of the object or the sample in the switched-off state of the illumination light source and the transmission in the switched-on state of the illumination light source by use of a sole detector. Further, it may be suitable to provide within the detector device a further detector for detecting the fluorescence radiation emitted by the object.

It is particularly preferred that the device of the invention is realized on the basis of a commercially available laser scanning microscope. The latter can be e.g. an LSM module of the type Olympus Fluo View, or a confocal Nipkow scanning module of the type Yokogawa CSU-10, which are respectively attached to a common optical light microscope, e.g. from the type series Olympus IX-70.

In the device of the invention, the illumination light source is preferably arranged opposite the excitation light source, i.e. on the opposite side of the object. The illumination light source is preferably a wide-range light source whose radiation is guided onto the object e.g. by a condenser as commonly used in microscopes. In this case, the detection of the preferably transmitted radiation emitted by the object is performed on the same side of the object where the excitation light source is arranged. Then, preferably, there is provided an at least partially common optics system for guiding the excitation radiation onto the object as well as for guiding the transmitted illumination radiation to the detector means. Upstream of the detector device, a color filter, particularly a band pass filter, can be arranged.

Preferably, the radiation exciting the measurement volume is divergent; with particular preference, a numerical aperture is provided for this radiation, which substantially corresponds to the numerical aperture of the detector optics. It is thus accomplished that the detection of the transmitted light, by being performed via a pinhole or the like, is given a weighting function which will prefer the desired object plane that is to be observed.

According to a preferred embodiment of the method of the invention which is preferably performed by the above described device of the invention, it is provided that, in a first step, the illumination radiation transmitted through the object is measured at a first intensity of the excitation radiation. Through a second measurement, the transmitted illumination radiation is measured at a second intensity of the excitation radiation. Thereafter, a comparison is performed between the two measurement values, particularly between the intensity values of the illumination radiation transmitted through the corresponding measurement volumes. Alternatively, it can be provided that the intensity of the excitation radiation is modulated at a rate which is larger than the scanning rate of the scan process, and that the amplitude of the variations of the intensity transmitted through the object can be detected by the detector.

A possible application of the device of the invention resides in the examination of the transmission properties of objects. For this purpose, the sample is illuminated both by an excitation light source, also referred to as a pump light source, and by an illumination light source, also referred to as a sample light source. In the process, the molecules of the object under investigation are excited by the excitation light source so that the population density of the basic condition of the molecule is reduced. As a result, the light coming from the illumination light source, and an electromagnetic radiation, respectively, will not excite the molecules anymore but will pass through the object, so that the transmission can be measured. In doing so, the two light sources, which can be laser light sources, are operated with similar wavelength regions, wherein the light can be visible or non-visible light. In the methods known from the state of the art, both the illumination light source and the excitation light source are focused onto the same site of the object whereas the method of the invention is related to a spatially dimensioned illumination of a portion of the object. Nonetheless, according to the invention, it is possible to examine the transmission properties of the object with precise spatial resolution, particularly in a confocal manner. For this purpose, the focused excitation radiation is used for a spatially resolved modulating or influencing of the transmission properties. Preferably, the s detector can be arranged confocally to the foci of the excitation radiation; particularly, the excitation radiation and the detected radiation can be guided through the same pinhole systems since the excitation light source and the detector can be arranged on the same side relative to the object. In the methods known from the state of the art, however, obtaining a confocal detection requires that the foci of the illumination light source and the detector device, which are arranged on the same side relative to the object, are brought into precise congruence, which is possible only with high expenditure.

A further possible application of the invention resides in the analysis of two-stage absorption processes. In doing so, the molecules excited by the excitation radiation can be brought into a further excitation state by absorption of a further photon. This process can be verified through the absorption of the illumination radiation. If the molecules excited by the excitation radiation are excited, by absorption of a further photon of the illumination radiation, into a condition with autofluorescence, the fluorescence of this condition can be measured by suitable spectral filtration, particularly in a manner which is free of the signal background of the excitation radiation. Depending on the involved energy levels of the molecules, the wavelength of the measured frequencies can be larger or smaller than the excitation and/or illumination radiation.

A special example of two-stage absorption processes is a stimulated emission. In stimulated emission, the molecules excited by the excitation radiation will be excited by the illumination radiation for emission of a photon. The stimulated radiation normally has the same properties as the stimulating illumination photon, e.g. with respect to the wavelength, the direction and the polarization. The illumination wavelength preferably lies in the emission range of the excited molecules. As a possibility for verification, use can be made either of the apparent negative absorption of the illumination radiation, or of the reduction of fluorescence in other ranges of the emission.

Further, the device of the invention makes it possible to measure local concentrations of absorbing molecules, particularly colorant molecules. As compared to the known measurement of the fluorescence intensity, the measurement of the absorption as proposed herein offers the advantage of being largely independent of the emission properties of the molecules, which properties are in practice often influenced or adulterated by the chemical environment of the molecules.

A further method among the preferred methods which can be carried out particularly with the aid of the above described device of the invention, is the determining of the transmission change in dependence of the properties of the illumination radiation, e.g. by taking a plurality of transmission pictures at different illumination radiation intensities or illumination radiation wavelengths. Further, a change of fluorescence with respect to the influence of the illumination radiation can be determined by the modulation of the illumination radiation. In this case, if desired, it can be provided that the variation of the transmitted intensity is detected.

A further possible application resides in the spectral scanning of the excitation or illumination radiation. In this case, an absorption depending on the wavelength is indicated. This dependency can be used for evidencing e.g. the concentration relationships of different sorts of absorption molecules. In this manner, the change of the spectral distribution of the fluorescence light, of the intensity of the fluorescence light generated by a two-stage process or of the intensity of the stimulated emission can measured in dependence on the wavelength of the illumination radiation.

Further, with the aid of the device of the invention, it is possible to determine the lifespan of excited conditions of the absorbing molecules. For this purpose, use is made of illumination and/or excitation radiation which is pulsed and/or modulated in another manner. Particularly suited for this determination is the phase shift between periodically modulated excitation and illumination intensity. The transmitted illumination radiation will be captured by a detector in dependence on the phase shift. In this application, use can be made of a detector with relatively low time resolution.

There exist different methods for the separation of the radiation which is to be detected (e.g. the transmitted illumination radiation) and the excitation radiation. This can be performed e.g. by wavelength coding if the excitation radiation and the detection radiation have distinctly different wavelengths. The detection will then be realized by a dichroic beam splitter.

By the provision of illumination and/or excitation radiation which is e.g. pulsed or modulated in another manner, it is possible to achieve a temporal separation between effects caused by the illumination radiation and/or the excitation radiation. This can be carried out particularly with the aid of time-resolving detector devices.

Further, one can perform a separation of the transmitted illumination and excitation radiation by means of angle coding in the object plane. In this case, the excitation radiation and the illumination radiation will exit from the measurement volume in different spatial directions. If desired, the detection optics will be adjusted, by use of suitable apertures, to capture only the transmitted illumination radiation.

BRIEF DESCRIPTION OF THE DRAWINGS

Preferred embodiments of the invention will be described in greater detail hereunder with reference to the accompanying drawings.

In the drawings.

DETAILED DESCRIPTION OF THE PREFERRED EMBODIMENT

Figure 1:
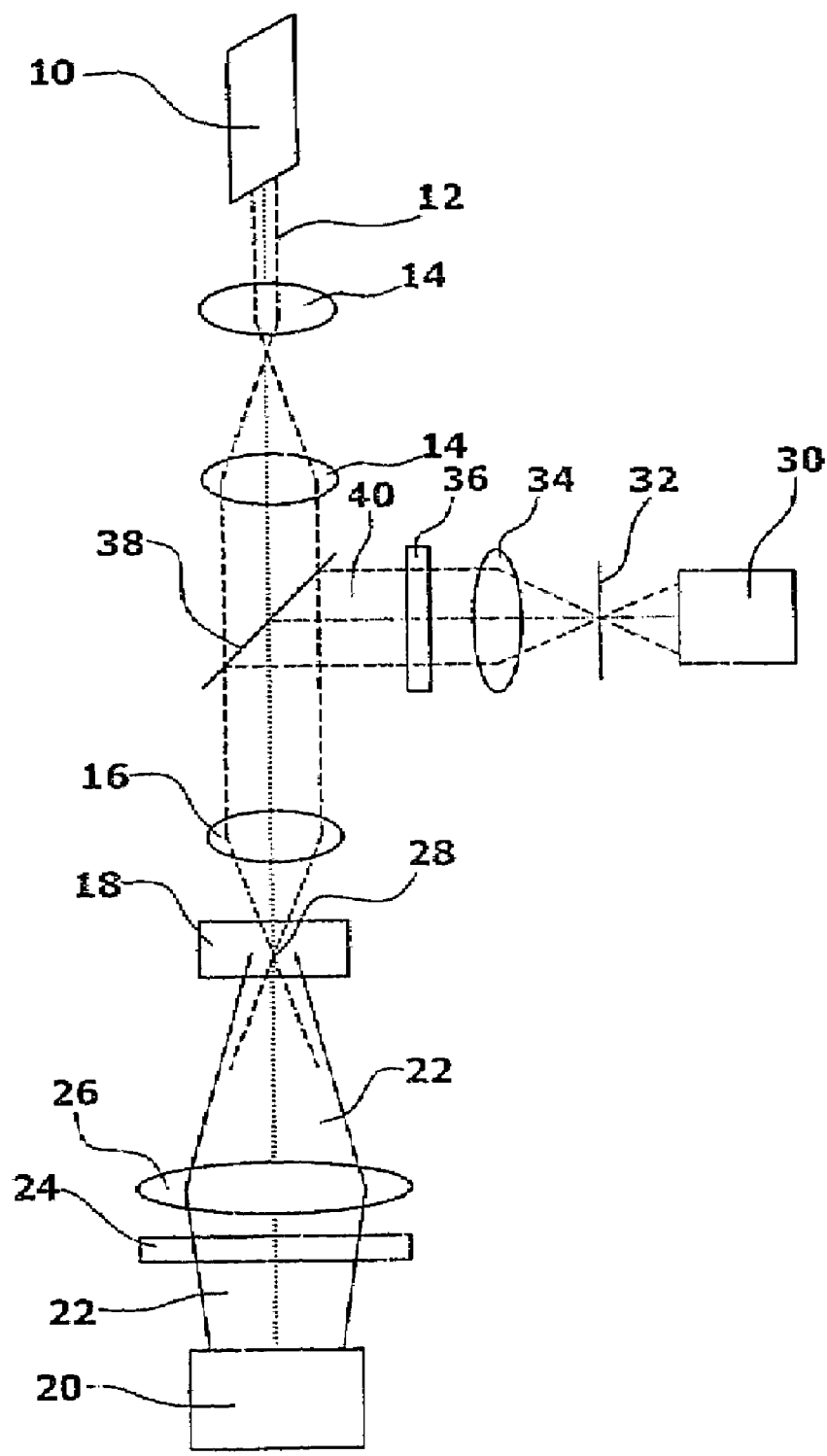
FIG. 1 is a schematic view of a first preferred embodiment of the device according to the invention.

The device comprises an excitation light source 10 whose excitation light beam is collimated by an optics device 14. By means of a further optics device 16, the excitation beam is focused within an object 18 which is particularly a chemical and/or optical sample which particularly comprises particles such as e.g. cells. The focus or the foci of the excitation radiation will determine the site of one or a plurality of measurement volumes 28 within the object.

For performing the measurement of optical properties of an object, particularly for performing transmission measurements, an illumination light source 20 is provided on the side of the object 18 opposite from the excitation light source. In the presently described embodiment, the illumination radiation issuing from illumination light source 20 has a different wavelength from that of the excitation light. The illumination beam 22 will pass through a color filter 24, if provided, and an optics device 26 which is preferably a condenser. Thereby, the illumination beam 22 is guided in the direction of the object but is not focused onto the measurement volume or volumes within the object 18. Instead, the illumination light source 20 will illuminate the object within an object portion to be observed, which object portion can have arranged therein a plurality of measurement volumes 28 corresponding to different foci of the excitation light source (FIG. 2).

Further, on the side of the excitation light source 10, there is provided a detector device 30 preferably in the form of a CCD array or a CCD camera. Arranged in front of the detector device is a pinhole 32 via which the measurement volume 28 is confocally imaged onto the detector device 30. For this purpose, an optics device 34 and, if required, a color filter 36 are arranged upstream of pinhole 32. The color filter 36, which is particularly provided as a bandpass filter, guarantees that the detector device 30 will substantially capture the radiation of illumination light source 20 transmitted by the object 28. Preferably, a suitable wavelength-dependent beam splitter 38 is selected for separating the excitation beam path 12 and the detection beam path 40.

The confocal optical arrangement of the excitation light source 10 and the detector device 30 allows for a three-dimensional spatially resolving measurement of the transmission change of individual measurement volumes 28 in the object 18 which is effected by the excitation light source 10. Here, the illumination radiation 22 whose transmission is measured through the object 18, does not have to be spatially resolving or confocal.

Figure 2:
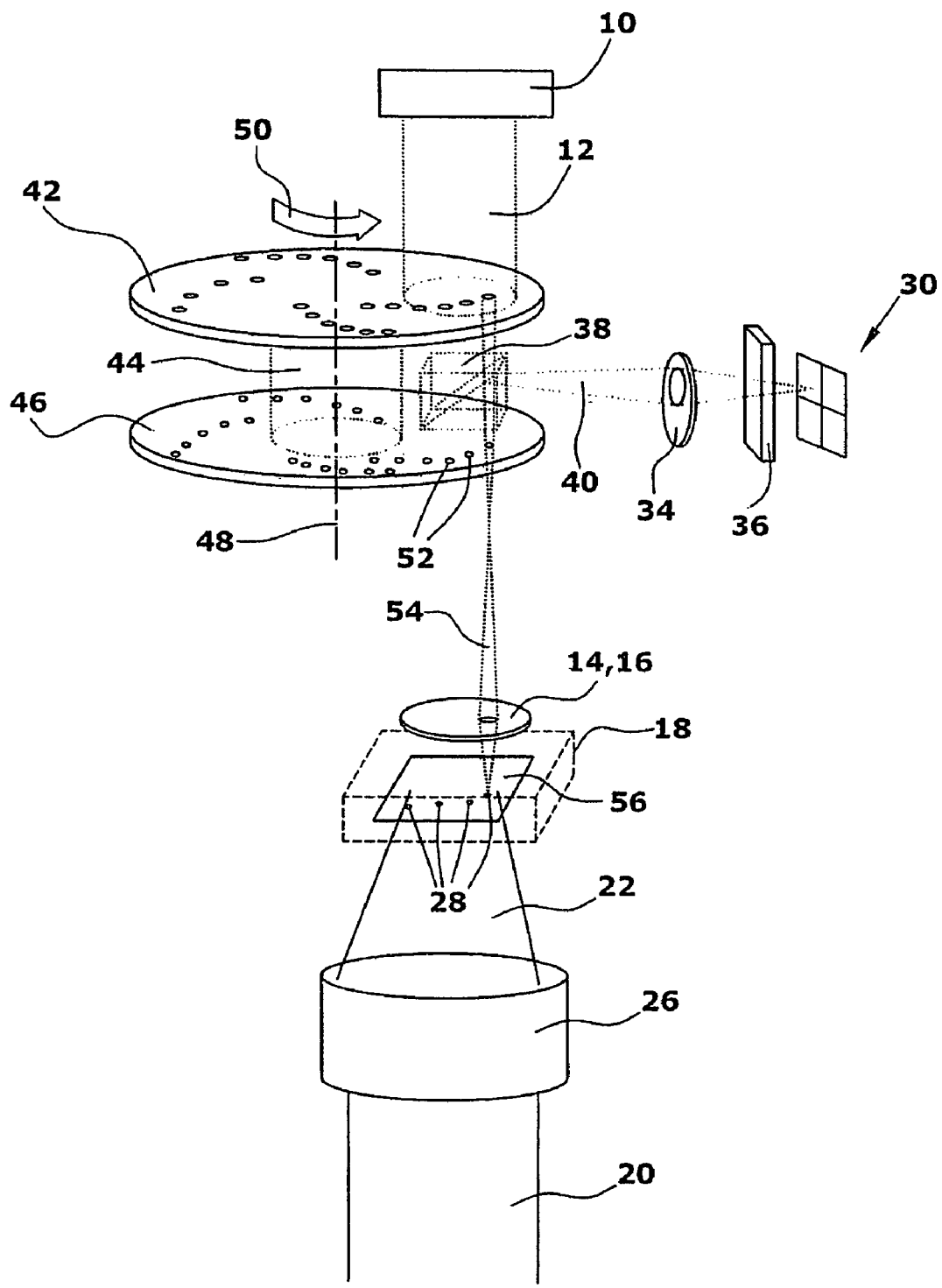
FIG. 2 is a schematic perspective view of a second preferred embodiment of the device according to the invention, showing only the essential components.

Instead of using a sole measurement volume 28 within the object 18, it is also possible to generate a plurality of foci in the object or the sample by means of a Nipkow module (FIG. 2).

For this purpose, the Nipkow module comprises a pinhole array 46. The collimated excitation beam 12 illuminates a plurality of pinholes 52, preferably several hundreds to thousands, at the same time. For increasing the excitation frequency, the pinhole array 46 in the illustrated example has a microlens array 42 arranged before it, with the lenses of the array focusing the excitation radiation onto the corresponding pinholes. Between the two disks 42,46, the wavelength-selective beam splitter 38 is arranged.

Via a connection element 44, the microlens array 42 is connected to a pinhole array 46. Both corresponding arrays can be rotated about a common longitudinal axis 48 in the direction of an arrow 50. By the rotation, the individual pinholes 52 will move on circular paths through the field of view. The plurality of pinholes 52 will thus scan the object 18 along a group of parallel circular segments.

FIG. 2 is an exemplary representation of the further course of the path of rays 54 coming from an individual pinhole. Actually, the plurality of the parallel paths of rays 54 passing through the individual pinholes 52 are focused by an optics device 16 into the object 18, whereby a plurality of measurement volumes 28 are generated within object 18. The measurement volumes 28 lie within an object plane 56 of object 18. The object plane 56 is illuminated within an object portion by an illumination beam 22.

The detection beam 40 deflected by the beam splitter 38 is guided to the detector device 30 via a lens 34 and a filter 36. Different from the normal use of a Nipkow module in a fluorescence microscope, the filter 36 in the present arrangement is selected to the effect that not the fluorescence excited by the excitation light 12 but the illumination light 22 transmitted through the object 18 will be detected. Thus, using a substantially unmodified Nipkow fluorescence microscope, the parallelizing of a plurality of measurement volumes 28 makes it possible to perform a fast confocal absorption measurement.

An exemplary embodiment of the device of the invention, which substantially corresponds to the arrangement illustrated in FIG. 2, will be described hereunder.

As an optomechanical base, use is made of an inverse microscope stand Olympus IX70. Arranged on a lateral port of this stand is a Nipkow module Yokogawa CSU-100, serving for confocal excitation and detection. As an excitation light source, use is made of a solid state laser Coherent Sapphire 488-20 emitting an excitation radiation having a wavelength of 488 nm. Adjustable neutral density filters and apertures allow the varying of the intensity of the excitation light. This radiation is coupled into the Nipkow module via an optical fiber. Internally of the module, the excitation radiation is collimated and guided through microlens and pinhole disks rotating as a unit. The pinhole array is imaged into the sample via a tube lens, provided as a standard feature in the IX70 microscope stand, as well as an objective of the type Olympus UPIApo 20× (numerical aperture 0.7; water immersion). In the present case, the samples under examination are particularly cells marked by fluorescent colorants, which cells are sedimented on the bottom of a microtitering plate. The usual commercially available micro-titering plate comprises a grid of 96 or 384 sample vessels. The bottom of the microtitering plate is provided as an optically transparent film with good transmission properties and good planarity; suitable microtitering plates are e.g. those of the type Greiner uclear. Above the cells, a buffering liquid is arranged. The sample carrier is open towards the top.

The light issuing from the sample will then be imaged through the same objective onto the pinhole disk. By means of dichroic beam splitter arranged internally of the Nipkow module between the pinhole and microlens disks, this light will then be mirrored in the direction of a CCD detector. This beam splitter is designed to transmit the wavelength range of 480-495 nm which includes the excitation light. Particularly, the beam splitter reflects the wavelength range of 495-600 which is to be used for analyzing the radiation issuing from the sample. The CCD detector can be a CCD camera of the type PCO Sensicam QE which, due to the Peltier cooling of the CCD sensor, offers a particularly high signal/noise ratio. Arranged between the dichroic beam splitter and the CDD detector is a lens system comprising collimation and imaging lenses; this lens system is operative to effect an imaging of the pinhole disk onto the CCD detector. For selection of the wavelength range to be detected, exchangeable band pass filters provided as dielectric multi-layered systems are arranged upstream of the CCD detector.

While the objective to be used for excitation and detection is arranged below the sample, an illumination device is arranged above the sample. The illumination device comprises an illumination light source TILL Photonics Polychrome IV which is spectrally variable by an integrated grid spectrometer. The emitted spectrally filtered light is supplied to the sample via a multimode light-conducting fiber and a condenser included in the commercial package. By the condenser, the illumination light is bundled only approximately onto the diameter of an individual sample vessel. The weakly convergent light cone can be guided through the curved meniscus of the exposed liquid surface towards the sedimented cells without noteworthy disturbance.

For fluorescence marking of the cells in the sample, use is made of a colorant which is absorbing in the wavelength range of about 480-510 nm and which can emit fluorescent light in the range of about 520-590 nm. The illumination light source is operated at a wavelength of 500 nm. To perform transmission measurements, photographs are taken of the sample by use of the CCD detector at different intensities of the excitation light within the wavelength range of the illumination light.

At a low intensity of the excitation light, only few colorant molecules in the sample are in the excited condition; most of them will be in the basic condition. The numerous non-excited colorant molecules are capable of absorbing the illumination light. Those sites on the image of the transmitted illumination light where a large number of colorant molecules exist in the sample, will have a low intensity.

For increasing the excitation performance, a major portion of the colorant molecules in the sample is in the excited state, i.e. is not capable anymore to absorb the illumination light. Concerning the transmitted light, the difference between sample regions of high and low colorant concentrations is smaller, and also the differences in brightness on the images of the CCD detectors are small. As a result of the considerable parallelization made possible by the solution presented by the invention, one can realize very brief exposure times of less than 1 sec for a complete confocal screening of the image portion.

A comparison between the site-dependent image brightness at different performance levels of the excitation light allows for conclusions on the local concentration of the colorant molecules.

Additionally, it is possible to generate images in the wavelength range of the excited fluorescence of the colorant molecules. For this purpose, the illumination light source can be switched off, if required, and a bandpass filter for the wavelength range of 520-590 nm can be arranged upstream of the detector.

The fluorescence intensity of the sample, as determined in a site-dependent manner, can be compared with the transmission properties measured in a site-dependent manner. Since the emission efficiency of the colorant molecules is often heavily dependent on the chemical properties, such as the pH value, of the surrounding sample liquid, this comparison will yield information on the local chemical properties of the cells in the sample.

The invention claimed is:

1. A device for measuring optical properties of an object, comprising:
   an illumination light source illuminating the object, said illumination light source emitting illumination radiation,
   an excitation light source illuminating the object, said excitation light source emitting excitation radiation being suited to change the optical properties of the object,
   a detector device detecting radiation issuing from the object,
   means for imaging at least one measurement volume substantially lying in an object plane located within the object, onto the detector device, wherein said detector device has a spectral sensitivity for detection of the illumination radiation passing through the object, wherein said detector device is arranged confocally to the measurement volume or the measurement volumes,
   said illumination light source illuminating a spatially dimensioned object portion, and the excitation radiation of the excitation light source being focused into the at least one measurement volume.

2. The device according to claim 1, wherein said detector device has fluorescence radiation generated within the object.

3. The device according to claim 1, wherein said illumination light source and the excitation light source are arranged on opposite sides relative to the object.

4. The device according to claim 1, wherein said detector device is arranged on the same side as the excitation light source relative to the object.

5. The device according to claim 1, wherein said at least one measurement volume is substantially dot-shaped.

6. The device according to claim 1, wherein said measurement volume is substantially line-shaped.

7. The device according to claim 1, further comprising a pinhole array, that generates a plurality of measurement volumes.

8. The device according to claim 1, wherein at least one of the excitation light source and the illumination light source is at least one of spectrally variable and spectrally selectable.

9. The device according to claim 1, wherein at least one of said excitation light source and said illumination light source is variable in its radiation intensity.

10. The device according to claim 1 further comprising an optics device arranged between the object and the illumination light source and configured to cause the illumination radiation to issue through a numerical aperture of at least 0.1 from the object in the direction of the detector device.

11. The device according to claim 1, wherein said detector device comprises a plurality of detectors differing from each other with respect to their spectral sensitivity.

12. The device according to claim 1, wherein at least one of said illumination light source and said excitation light source are configured to emit intensity-modulated and particularly pulsed radiation.

13. A method for measuring optical properties of an object, comprising
   illuminating the object by an illumination light source,
   illuminating the object by an excitation light source emitting excitation radiation suited to change the optical properties of the object,
   detecting the radiation issuing from the object by use of a detector device,
   imaging at least one measurement volume substantially lying in an object plane located within the object, onto the detector device, said illumination light source illuminating a spatially dimensioned object portion, and
   the excitation radiation of the excitation light source being focused into the at least one measurement.

14. The method according to claim 13, wherein said radiation issuing from the object is detected first while the object is illuminated with a first intensity of the illumination radiation and then while the object is illuminated with at least a second intensity of the illumination radiation.

15. The method according to claim 13, wherein the object is illuminated by intensity-modulated and particularly pulsed excitation radiation and detection is performed preferably of the temporal variation of the intensity of the radiation detected by the detector device.

16. The method according to claim 15, wherein the object is illuminated by intensity-modulated illumination radiation and detection is performed by the intensity of the radiation detected by the detector device in dependence on the phase difference between the intensity modulations of the excitation and illumination radiation.

17. The method according to claim 13, wherein the sensitivity of the detector device is modulated.

* * * * *